United States Patent
Ohno et al.

(10) Patent No.: US 10,371,645 B2
(45) Date of Patent: Aug. 6, 2019

(54) OPTICAL PROCESSING HEAD, OPTICAL PROCESSING APPARATUS, AND CONTROL METHOD AND CONTROL PROGRAM OF OPTICAL PROCESSING APPARATUS

(71) Applicant: TECHNOLOGY RESEARCH ASSOCIATION FOR FUTURE ADDITIVE MANUFACTURING, Tokyo (JP)

(72) Inventors: Hiroshi Ohno, Yokohama (JP); Yuji Sasaki, Yokohama (JP); Mitsuo Sasaki, Yokohama (JP); Takashi Obara, Yokohama (JP); Kazuyuki Masukawa, Yokohama (JP)

(73) Assignee: TECHNOLOGY RESEARCH ASSOCIATION FOR FUTURE ADDITIVE MANUFACTURING, Tokyo (JP)

( * ) Notice: Subject to any disclaimer, the term of this patent is extended or adjusted under 35 U.S.C. 154(b) by 383 days.

(21) Appl. No.: 14/888,281

(22) PCT Filed: Mar. 10, 2015

(86) PCT No.: PCT/JP2015/057074
§ 371 (c)(1),
(2) Date: Oct. 30, 2015

(87) PCT Pub. No.: WO2016/143083
PCT Pub. Date: Sep. 15, 2016

(65) Prior Publication Data
US 2017/0045462 A1    Feb. 16, 2017

(51) Int. Cl.
*G01N 21/94*    (2006.01)
*G01N 21/15*    (2006.01)
(Continued)

(52) U.S. Cl.
CPC .............. *G01N 21/94* (2013.01); *B23K 26/03* (2013.01); *B23K 26/0643* (2013.01);
(Continued)

(58) Field of Classification Search
CPC .............. B23K 26/032; B23K 26/0736; B23K 26/0648; B23K 26/1476; B23K 26/0665;
(Continued)

(56) References Cited

U.S. PATENT DOCUMENTS 3,705,771 A * 12/1972 Friedman ........... G01N 15/1434
250/461.2
3,988,068 A * 10/1976 Sprague ............. G01M 11/0278
356/124

(Continued)

FOREIGN PATENT DOCUMENTS

DE    10 2008 015 133 A1    9/2009
DE    102008015133 A1 *    9/2009    ........... B23K 26/032

(Continued)

OTHER PUBLICATIONS

Pittl et al., "Apparatus for collecting process light during laser machining", Sep. 2009, DE-102008015133, Machine Translation (Year: 2009).*

(Continued)

*Primary Examiner* — Michael E Barr
*Assistant Examiner* — Thomas Bucci
(74) *Attorney, Agent, or Firm* — Ladas & Parry LLP (57) ABSTRACT

An optical processing head that detects a trouble of an optical processing head that will be generated at the time of optical processing before the trouble occurs is disclosed. The optical processing head that performs processing by condensing, on a process surface, a ray emitted by a light source for processing includes a cylindrical housing that surrounds a ray for processing emitted by the light source for process- (Continued)

ing, a ray emitter for inspection that is incorporated in the cylindrical housing and arranged outside the path of the ray for processing, and a light receiver that is incorporated in the cylindrical housing, arranged outside the path of the ray for processing, and receives a ray for inspection emitted by the ray emitter for inspection. The contamination of the inner surface of the cylindrical housing or the concentration of a scattering object flowing into the cylindrical housing is inspected by using a signal acquired from the light receiver.

10 Claims, 10 Drawing Sheets

(51) Int. Cl.
| | |
|---|---|
| *B23K 26/70* | (2014.01) |
| *B23K 26/03* | (2006.01) |
| *B23K 26/06* | (2014.01) |
| *B23K 26/14* | (2014.01) |
| *B23K 26/21* | (2014.01) |
| *G02B 5/08* | (2006.01) |
| *G02B 19/00* | (2006.01) |
| *G02B 27/00* | (2006.01) |
| *G01N 21/71* | (2006.01) |
| *G01N 21/954* | (2006.01) |
| *G01N 21/17* | (2006.01) |

(52) U.S. Cl.
CPC ...... *B23K 26/0648* (2013.01); *B23K 26/1476* (2013.01); *B23K 26/21* (2015.10); *B23K 26/707* (2015.10); *G01N 21/15* (2013.01); *G02B 5/08* (2013.01); *G02B 19/0052* (2013.01); *G02B 19/0076* (2013.01); *G02B 27/0006* (2013.01); *G01N 21/718* (2013.01); *G01N 21/954* (2013.01); *G01N 2021/1757* (2013.01)

(58) Field of Classification Search
CPC .... B23K 26/03; G01N 15/0205; G01N 21/15; G01N 21/0211; G01N 21/47; G01N 21/94; G01N 2021/157; G01N 21/532; G01N 21/65; G01N 2021/4709; G02B 19/0076; G02B 27/0006; G02B 19/0052; G02B 27/0955
USPC .......... 134/56 R, 1.1; 356/342, 239.2, 237.2, 356/336, 301, 337, 445, 124, 318, 73, 28, 356/237.1, 369, 237.3, 341, 442; 250/574, 573; 219/121.63, 121.6, 121.67, 219/121.83, 121.75
See application file for complete search history.

(56) References Cited

U.S. PATENT DOCUMENTS

| | | | | |
|---|---|---|---|---|
| 5,198,369 A * | 3/1993 | Itoh | ........................ | G01N 21/82 356/337 |
| 5,432,601 A * | 7/1995 | Tanaka | ................ | G01N 15/0205 250/574 |
| 5,486,676 A * | 1/1996 | Aleshin | ................ | B23K 26/144 219/121.63 |
| 5,662,822 A | 9/1997 | Tada et al. | | |
| 5,793,478 A * | 8/1998 | Rader | ........................ | G01F 1/661 356/28 |
| 5,835,220 A * | 11/1998 | Kazama | .................... | G01J 4/04 356/369 |
| 5,977,515 A | 11/1999 | Uraki et al. | | |
| 6,097,025 A * | 8/2000 | Modlin | ................ | G01N 21/253 250/205 |
| 6,271,916 B1 * | 8/2001 | Marxer | .............. | G01N 21/9501 356/237.3 |
| 6,522,386 B1 * | 2/2003 | Nishi | ................... | G03F 7/70241 355/52 |
| 6,778,271 B2 * | 8/2004 | Watson | .............. | G01N 15/0211 356/336 |
| 6,778,272 B2 * | 8/2004 | Nakano | ............. | H01J 37/32082 356/336 |
| 6,791,057 B1 * | 9/2004 | Kratzsch | ............... | B23K 26/032 219/121.62 |
| 7,084,970 B2 * | 8/2006 | Weiss | ..................... | G01N 21/95 356/237.4 |
| 7,151,603 B2 * | 12/2006 | Kellie | .................... | G01N 21/47 356/342 |
| 7,206,066 B2 * | 4/2007 | Vurens | .................. | G01N 21/211 356/237.2 |
| 7,428,041 B2 * | 9/2008 | Kallio | ................... | G01S 7/4812 356/4.01 |
| 7,656,526 B1 * | 2/2010 | Spuler | ................... | G01N 21/538 356/336 |
| 7,705,292 B2 * | 4/2010 | Hammann | ............. | G01K 11/24 250/221 |
| 7,821,636 B2 * | 10/2010 | Jeys | ..................... | G01B 11/002 250/573 |
| 7,920,261 B2 * | 4/2011 | Jeys | ................... | G01N 15/1434 356/338 |
| 8,319,965 B2 * | 11/2012 | Jeys | ..................... | G01B 11/002 250/573 |
| 8,334,972 B2 * | 12/2012 | Thien | ..................... | G01N 21/94 340/425.5 |
| 8,890,023 B2 * | 11/2014 | Dorsch | ................ | B23K 26/032 219/121.64 |
| 2004/0032649 A1 * | 2/2004 | Kondo | ................... | G03B 35/00 359/364 |
| 2004/0156052 A1 * | 8/2004 | Yamamoto | ............. | G01N 21/47 356/446 |
| 2006/0192968 A1 * | 8/2006 | Farrant | .................. | G01N 21/15 356/445 |
| 2007/0146705 A1 * | 6/2007 | Kaufmann | ........... | G01N 21/532 356/342 |
| 2008/0117419 A1 * | 5/2008 | Hays | ...................... | G01N 21/47 356/342 |
| 2008/0266666 A1 * | 10/2008 | Hughes | .............. | G02B 19/0095 359/618 |
| 2010/0247934 A1 | 9/2010 | Meyer et al. | | |
| 2012/0080611 A1 * | 4/2012 | Jones | .................... | G01J 1/0242 250/458.1 |
| 2014/0152986 A1 * | 6/2014 | Trainer | .............. | G01N 15/0205 356/336 |
| 2014/0346155 A1 * | 11/2014 | Jurca | .................. | B23K 26/032 219/121.74 |

FOREIGN PATENT DOCUMENTS

| | | |
|---|---|---|
| JP | 61-49689 U | 4/1986 |
| JP | 1-99792 A | 4/1989 |
| JP | 6-246466 A | 9/1994 |
| JP | 2003-117674 A | 4/2003 |
| JP | 2005-81399 A | 3/2005 |
| JP | 2005081399 A * | 3/2005 |
| JP | 2014-237150 A | 12/2014 |
| WO | 2004/068069 A1 | 8/2004 |

OTHER PUBLICATIONS

Shioji et al., "Method and apparatus for preventing contamination inside optical axis in laser machining apparatus", Mar. 2005, JP-2005081399, Machine Translation (Year: 2005).*
Extended European Search Report (ESR) for corresponding European Application No. 15 78 5041.3.
Espacenet English abstract of DE 10 2008 015 133 A1.
International Search Report (ISR) dated Jun. 17, 2015 for International Application No. PCT/JP2015/057074.
J-PlatPat English abstract of JP 1-99792 A.
J-PlatPat English abstract of JP 2005-81399 A.

(56) References Cited

OTHER PUBLICATIONS

J-PlatPat English abstract of JP 6-246466 A.
Japanese Office Action dated Aug. 25, 2016 for Japanese Application No. 2015-549109 with English translation.
J-PlatPat English abstract of JP 2003-117674 A.
J-PlatPat English abstract of JP 2014-237150 A.

* cited by examiner

OPTICAL PROCESSING HEAD, OPTICAL PROCESSING APPARATUS, AND CONTROL METHOD AND CONTROL PROGRAM OF OPTICAL PROCESSING APPARATUS

RELATED APPLICATION

This application is an application under 35 U.S.C. 371 of International Application No. PCT/JP2015/057074 filed on Mar. 10, 2015, the entire contents of which are incorporated herein by reference.

TECHNICAL FIELD

The present invention relates to an optical processing head, an optical processing apparatus, and a control method and control program of the optical processing apparatus.

BACKGROUND ART

In the above technical field, patent literature 1 discloses a method using the ultrasonic vibration in order to detect contamination of a lens by a fine particle (fume or sputter) generated at the time of processing.

CITATION LIST

Patent Literature

Patent literature 1: U.S. Pat. No. 7,705,292

SUMMARY OF THE INVENTION

Technical Problem

In the technique described in this literature, however, the lens slightly vibrates at the time of ultrasonic vibration. Along with this, a condensed spot also oscillates, decreasing the processing accuracy.

The present invention enables to provide a technique of solving the above-described problem.

Solution to Problem

One aspect of the present invention provides an optical processing head that performs processing by condensing, on a process surface, a ray emitted by a light source for processing, comprising:

a cylindrical housing that surrounds a ray for processing emitted by the light source for processing;

a ray emitter for inspection that is incorporated in the cylindrical housing and arranged outside a path of the ray for processing; and a light receiver that is incorporated in the cylindrical housing, arranged outside the path of the ray for processing, and receives a ray for inspection emitted by the ray emitter for inspection, wherein one of a contamination of an inner surface of the cylindrical housing and a concentration of a scattering object flowing into the cylindrical housing is inspected by using a signal acquired from the light receiver.

Another aspect of the present invention provides a method of controlling an optical processing apparatus that performs processing by condensing, on a process surface, a ray emitted by a light source for processing, the optical processing apparatus including:

a cylindrical housing that surrounds a ray for processing emitted by the light source for processing;

a ray emitter for inspection that is incorporated in the cylindrical housing and arranged outside a path of the ray for processing; and a light receiver that is incorporated in the cylindrical housing, arranged outside the path of the ray for processing, and receives a ray for inspection emitted by the ray emitter for inspection, the method comprising:

changing, based on the signal, an amount of a purge gas ejected to the process surface.

Still other aspect of the present invention provides a program of controlling an optical processing apparatus that performs processing by condensing, on a process surface, a ray emitted by a light source for processing, the optical processing apparatus including:

a cylindrical housing that surrounds a ray for processing emitted by the light source for processing;

a ray emitter for inspection that is incorporated in the cylindrical housing and arranged outside a path of the ray for processing; and a light receiver that is incorporated in the cylindrical housing, arranged outside the path of the ray for processing, and receives a ray for inspection emitted by the ray emitter for inspection, the program causing a computer to execute:

changing, based on the signal, an amount of a purge gas ejected to the process surface.

Advantageous Effects of Invention

The present invention can provide an optical processing technique capable of detecting a trouble of an optical processing head that will be generated at the time of optical processing, before the trouble occurs.

DESCRIPTION OF THE EMBODIMENTS

A preferred embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise. In the following embodiments, "light" includes various electromagnetic waves ranging from ultraviolet light to a microwave, and can be properly selected in accordance with a processing target or the like.

First Embodiment

Figure 1:
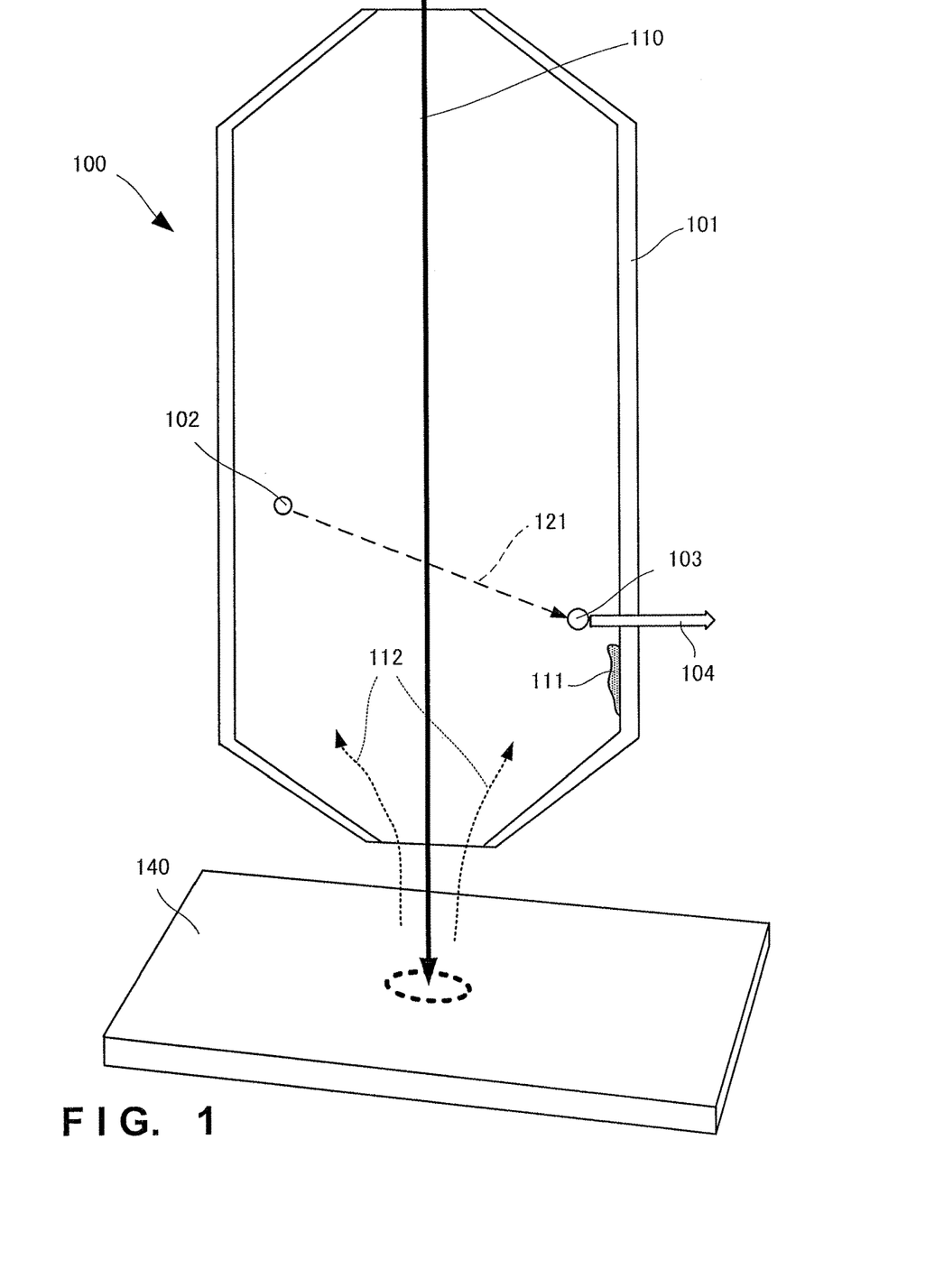
FIG. 1 is a view showing the arrangement of an optical processing head according to the first embodiment of the present invention.

An optical processing head 100 according to the first embodiment of the present invention will be described with reference to FIG. 1. FIG. 1 is a sectional view showing the optical processing head 100. The optical processing head 100 performs processing by condensing, on a process surface 140, a ray 110 emitted by a light source for processing (not shown).

The optical processing head 100 includes a cylindrical housing 101, a ray emitter 102 for inspection, and a light receiver 103.

The cylindrical housing 101 surrounds the ray 110 for processing emitted by the light source for processing. The ray emitter 102 for inspection is incorporated in the cylindrical housing 101 and arranged outside the path of the ray 110 for processing. The light receiver 103 is incorporated in the cylindrical housing 101, arranged outside the path of the ray 110 for processing, and receives a ray 121 for inspection emitted by the ray emitter 102 for inspection.

A contamination 111 of the inner surface of the cylindrical housing 101 or the concentration of a scattering object 112 flowing into the cylindrical housing 101 is inspected by using a signal 104 acquired from the light receiver 103. When the scattering object 112 flows into the cylindrical housing 101, it absorbs or scatters the ray 121 for inspection. As a result, the strength of the signal 104 decreases. That is, when the scattering object 112 is mixed, the signal 104 temporally changes, and the presence/absence of inflow of the scattering object 112 can be determined. When the contamination 111 is attached to the inner surface of the cylindrical housing 101, it absorbs the ray 121 for inspection, and the signal 104 becomes lower than a predetermined reference value. That is, the degree of contamination of the inner surface can be determined from a change of the signal 104 from a reference value.

The first embodiment can provide an optical processing technique in which, by detecting the contamination 111 on the inner surface of the cylindrical housing 101 or the concentration of the scattering object 112 flowing into the cylindrical housing 101, a trouble of the optical processing head that will be generated at the time of optical processing can be detected before the trouble occurs. In the present invention, the cylindrical housing 101 is not limited to a circular cylindrical shape, but suffices to have a cylindrical shape such as a square cylindrical shape, or another shape. The ray emitter 102 for inspection is not limited to a light source and may be the exit port of a light transmitting portion such as an optical fiber.

Second Embodiment

Figure 2:
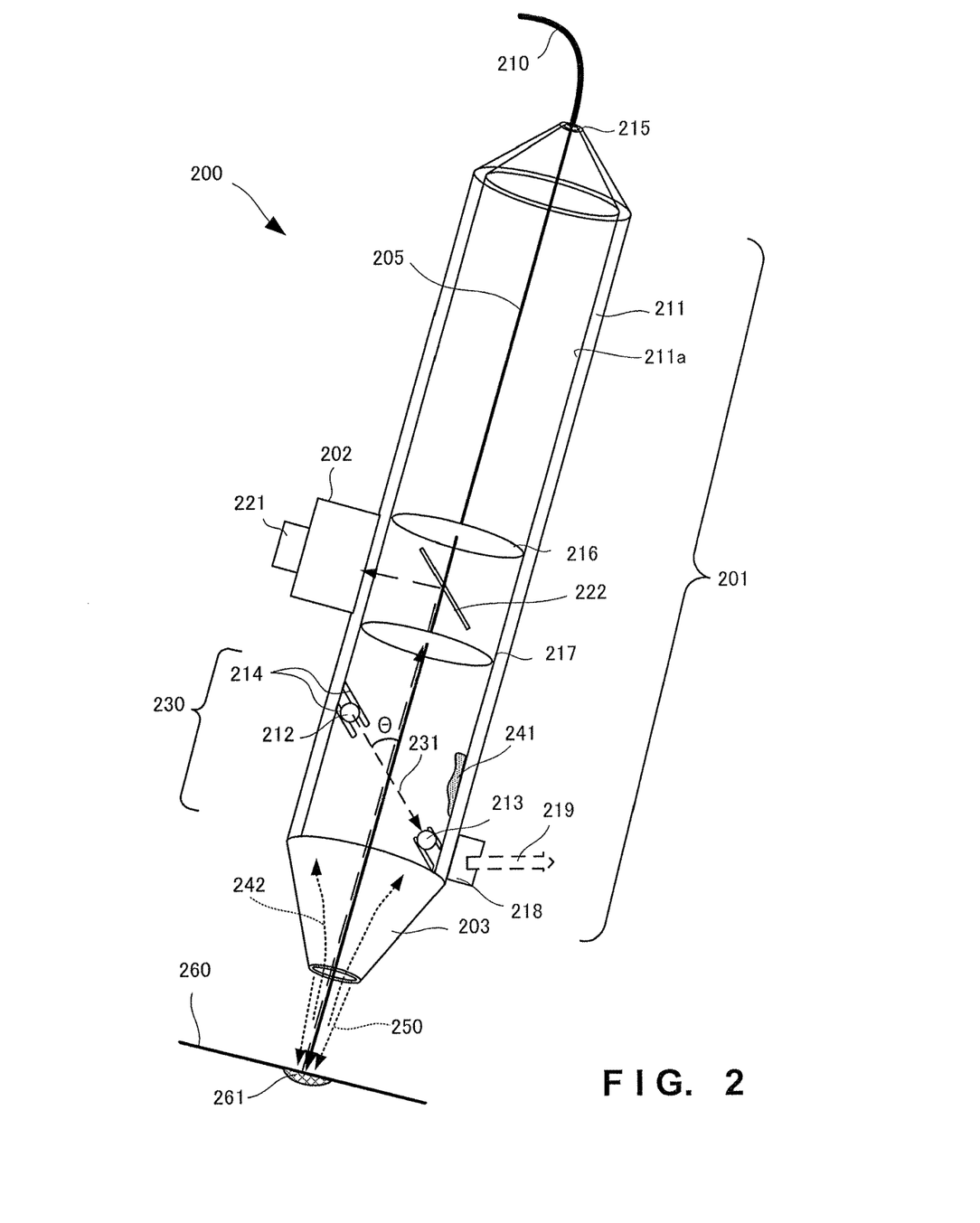
FIG. 2 is a perspective view showing the arrangement of an optical processing head according to the second embodiment of the present invention.

An optical processing head 200 according to the second embodiment of the present invention will be described with reference to FIG. 2. FIG. 2 is a view showing the internal arrangement of the optical processing head 200 to which a laser beam is applied. As shown in FIG. 2, the optical processing head 200 includes a condensing optical system device 201, an observation device 202, and a nozzle 203.

(Overall Arrangement of Head)

The condensing optical system device 201 is constituted by a collimator lens 216, a condenser lens 217, and a circular cylindrical housing 211 that holds them. The collimator lens 216 converts, into parallel light, a ray 205 for processing that travels from an incident end 215. The condenser lens 217 condenses the parallel light on a process surface 260 on the downstream side.

With these optical systems, the condensing optical system device 201 ejects, to the process surface 260, the ray 205 for processing that has been emitted by a light source (not shown), has passed through a light transmitting portion 210, and has been guided from the incident end 215. The light transmitting portion 210 is, for example, an optical fiber having a core diameter of φ0.01 to 1 mm, and guides light (for example, a laser beam) generated by the light source to the optical processing head 200.

The ray 205 for processing that has been guided from the incident end 215 to the optical processing head 200 comes out to the process surface 260, and forms a molten pool 261 on the process surface 260.

The nozzle 203 receives supply of a processing material and gas from a material supply device (not shown) through a material supply portion, and ejects a material 250 mixed in the gas to the molten pool 261 of the process surface 260. After that, the molten pool 261 is cooled and hardened to deposit the material on the process surface 260. The molten pool 261 is moved on the process surface 260, and melting, material supply, and cooling are repeated, implementing three-dimensional shaping.

The observation device 202 is a device for observing the status of processing by the condensing optical system device 201 from a viewpoint along the optical axis of the ray 205 for processing. The observation device 202 includes an image capturing device 221 including an image sensor such as a CCD or CMOS sensor, and a one-way mirror 222 that is provided inside the condensing optical system device 201 and serves as a mirror for observation. The surface of the one-way mirror 222 is coated so that the one-way mirror 222 transmits the ray 205 for processing (wavelength: 1,060 nm), but reflects visible light (wavelength: 450 to 800 nm). Part of visible light reflected by the process surface 260 is reflected by the one-way mirror 222 and guided to the image capturing device 221. By performing feedback control of processing parameters in accordance with the observed processing status, the processing accuracy can be improved.

A ray emitter 212 for inspection and a light receiver 213 are arranged downstream of the condenser lens 217. The ray emitter 212 for inspection is arranged upstream of the ray 205 for processing with respect to the light receiver 213. A ray 231 for inspection emitted by the ray emitter 212 for inspection neither reaches the one-way mirror 222 nor is captured by the image capturing device 221. That is, light emitted by the ray emitter 212 for inspection does not act as noise at the time of image capturing. In other words, there is an effect of reducing noise when the ray emitter 212 for inspection is arranged upstream of the light receiver 213. A shielding plate 214 is provided around the ray emitter 212 for inspection so as to prevent the ray 231 for inspection from becoming noise in the image capturing device 221. Hence, the ray for inspection that does not travel to the light receiver 213 is absorbed and cut off (Arrangement of Inspection Unit)

If a scattering object 242 called a fume or sputter scattering from the process surface 260 enters the inside of the circular cylindrical housing 211 at the time of processing, the optical system such as the condenser lens 217 is contaminated, and a contamination 241 is attached to a housing inner surface 211a, decreasing the light utilization efficiency. As an inspection unit 230 that inspects the influence of the scattering object 242, the circular cylindrical housing 211 of the optical processing head 200 incorporates the ray emitter 212 for inspection, the light receiver 213, the shielding plate 214, and a signal output portion 218.

The ray emitter 212 for inspection is, for example, an LED, and the wavelength is 400 to 450 nm. However, the ray emitter 212 for inspection is not limited to this, and may be a halogen lamp, an incandescent lamp, a krypton lamp, or the like. The wavelength is arbitrary as long as it is different from the wavelength of the ray 205 for processing (that is, the wavelength is arbitrary except for 1,060 nm). If the wavelength of the ray 231 for inspection and that of the ray 205 for processing differ from each other, the light receiver 213 does not mistake the ray 205 for processing, for the ray 231 for inspection. Noise of a detection signal can therefore be reduced.

The ray emitter 212 for inspection and the light receiver 213 are arranged to face each other outside the path of the ray 205 for processing. The light receiver 213 receives the ray 231 for inspection emitted by the ray emitter 212 for inspection, and transfers, to the signal output portion 218, a signal corresponding to the received light amount. When the scattering object 242 enters the path of the ray 231 for inspection, the amount of light received by the light receiver 213 temporarily decreases. When the scattering object 242 is attached as the contamination 241 to the housing inner surface 211a, the amount of light received by the light receiver 213 continuously decreases.

Thus, the influence of the scattering object 242 is detected by detecting the presence/absence of a temporal change (temporary fluctuation and/or continuous decrease from a reference value by a predetermined amount or more) of the amount of light received by the light receiver 213. By using the signal acquired from the light receiver 213, the signal output portion 218 outputs a signal 219 representing the contamination 241 of the inner surface of the circular cylindrical housing 211 or the concentration of the scattering object 242 flowing into the nozzle 203 and the circular cylindrical housing 211. The concentration of scattering object is considered to be higher as a change of the light amount is larger. That is, the concentration of the scattering object can be inspected based on the magnitude of a change of the light amount.

In this manner, a trouble (degradation of the quality caused by contamination of the condenser lens) of the optical processing head that is generated at the time of optical processing can be detected by inspecting the contamination 241 of the inner surface of the circular cylindrical housing 211 or the concentration of the scattering object 242 flowing into the circular cylindrical housing 211. Decisive degradation of the quality of the optical processing head 200 can be avoided by, for example, a method of increasing the purge to prevent mixing of the scattering object.

Figure 3:
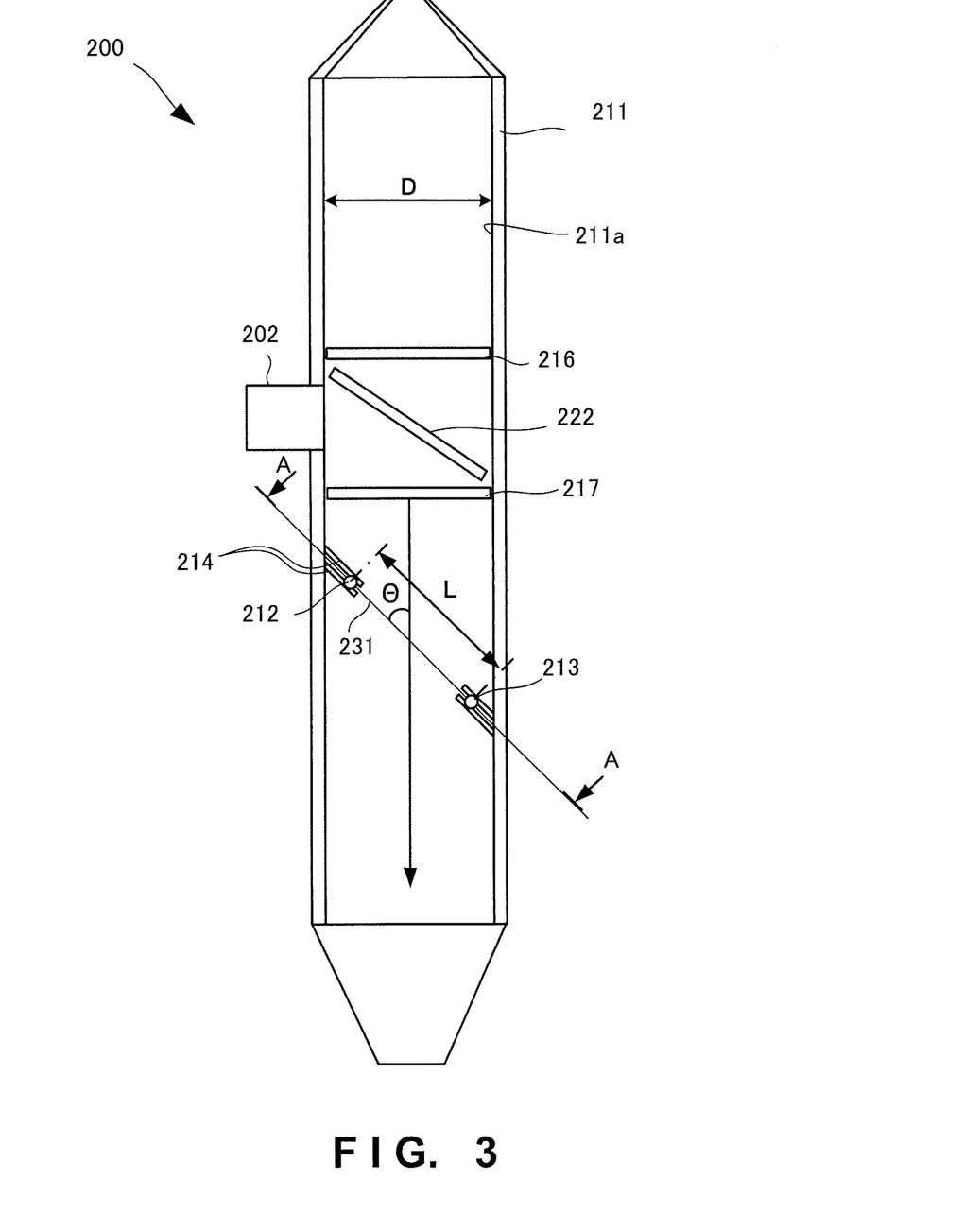
FIG. 3 is a sectional view showing the arrangement of the optical processing head according to the second embodiment of the present invention.
Figure 4:
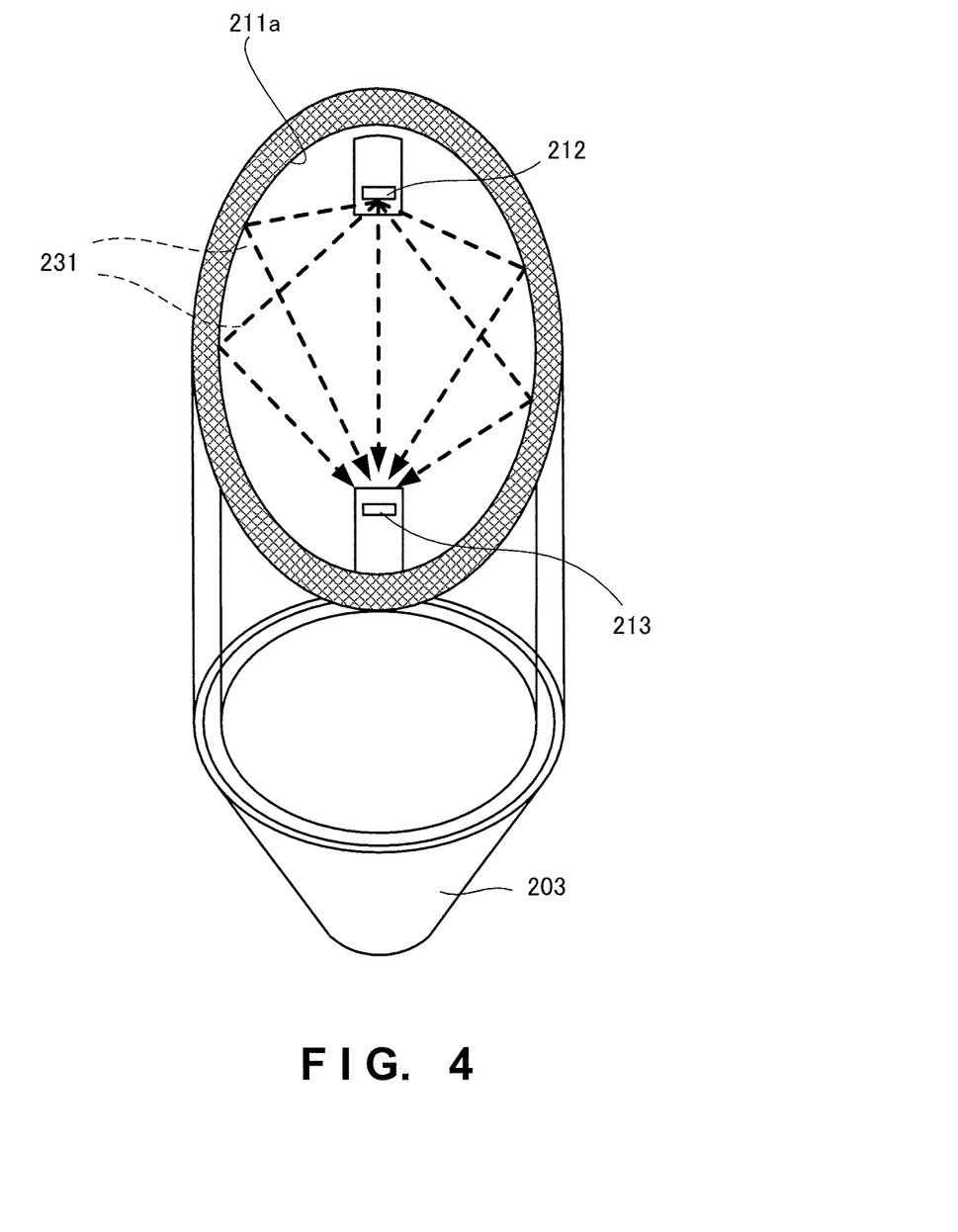
FIG. 4 is a sectional view showing the arrangement of a ray emitter for inspection and a light receiver, and a ray path between them according to the second embodiment of the present invention.

Next, the arrangement of the ray emitter 212 for inspection and the light receiver 213 will be described in detail with reference to FIGS. 3 to 5. FIG. 3 is a sectional view on a plane passing through the optical axis of the ray 205 for processing in the optical processing head 200. FIG. 4 is a sectional view taken along a line A-A in FIG. 3. The A-A section is a plane that is perpendicular to the optical axis of the ray 205 for processing and passes through the ray emitter 212 for inspection and the light receiver 213.

As is apparent from FIG. 4, the housing inner surface 211a draws an ellipse on the section passing through both the ray emitter 212 for inspection and the light receiver 213. The ray emitter 212 for inspection and the light receiver 213 are arranged at two focus positions of this ellipse. As is apparent from FIG. 4, the ray 231 for inspection emitted by the ray emitter 212 for inspection is reflected by the housing inner surface 211a, and almost all the ray 231 for inspection is collected to the light receiver 213.

As shown in FIG. 3, θ represents the angle of inclination, from the optical axis of the ray 205 for processing, of a line segment connecting the ray emitter 212 for inspection and the light receiver 213. L represents the distance (length of the line segment) between the ray emitter 212 for inspection and the light receiver 213. In this embodiment, the housing inner surface 211a has a columnar shape (columnar side surface) whose center axis is the optical axis of the ray 205 for processing. D represents the diameter of this column.

When θ, L, and D defined in the above way satisfy equation (1), the ray emitter 212 for inspection and the light receiver 213 can be arranged at the two focuses of the ellipse:

$$D/L = 2/\tan\theta \quad (1)$$

That is, equation (1) is a condition for arranging the ray emitter 212 for inspection and the light receiver 213 at the two focuses of the ellipse.

Theoretically, the light receiver 213 receives all the ray 231 for inspection emitted by the ray emitter 212 for inspection arranged to satisfy equation (1). In contrast, when the relation of equation (1) is not satisfied, a ray not received by the light receiver 213 exists.

Figure 5:
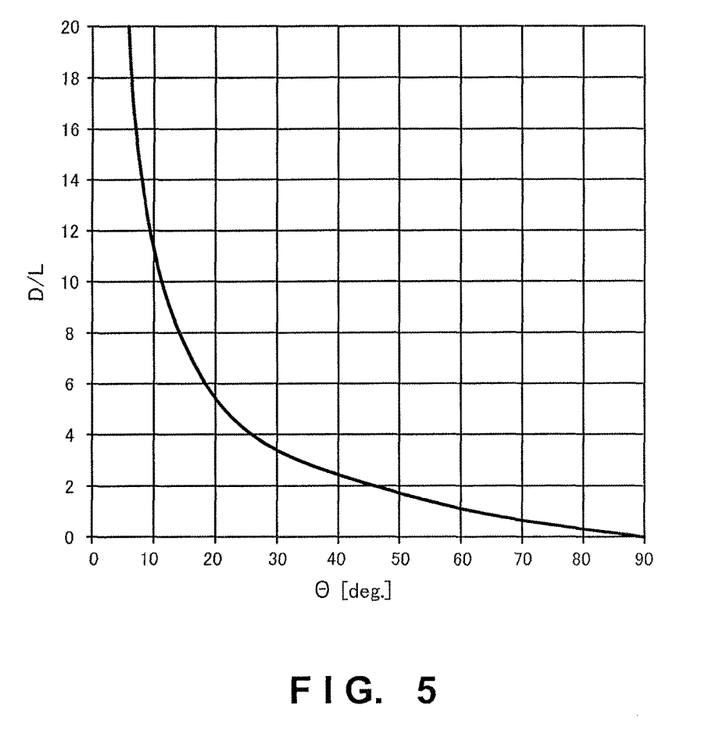
FIG. 5 is a graph showing the arrangement relation between the ray emitter for inspection and the light receiver according to the second embodiment of the present invention.

FIG. 5 shows the relation of equation (1). The abscissa represents the inclination angle θ, and the ordinate represents D/L. When θ=45°, D/L becomes about 2.

As described above, the second embodiment can provide an optical processing technique in which a trouble of the optical processing head that will be generated at the time of optical processing can be detected before the trouble occurs, by inspecting the contamination 241 of the inner surface of the circular cylindrical housing 211 or the concentration of the scattering object 242 flowing into the circular cylindrical housing 211.

Although the housing inner surface 211a has a shape conforming to the outer surface of the column in the above-described embodiment, the present invention is not limited to this. However, it is desirable that at least part of the housing inner surface 211a of the circular cylindrical housing 211 is a curved surface so that the ray 231 for inspection is reflected by the housing inner surface 211a of the circular cylindrical housing 211 and condensed to the light receiver 213.

Third Embodiment

Figure 6:
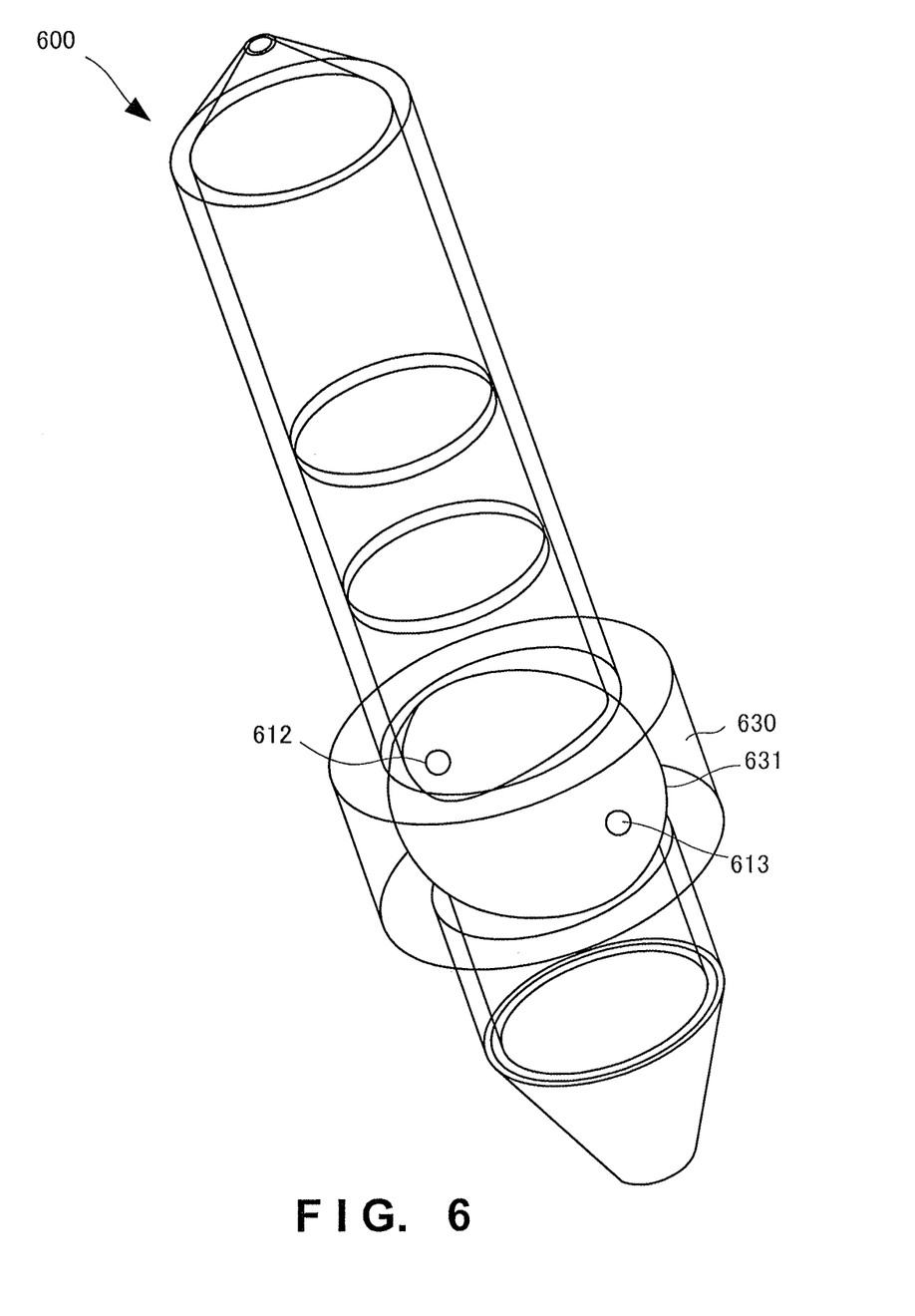
FIG. 6 is a perspective view showing the arrangement of an optical processing head according to the third embodiment of the present invention.
Figure 7:
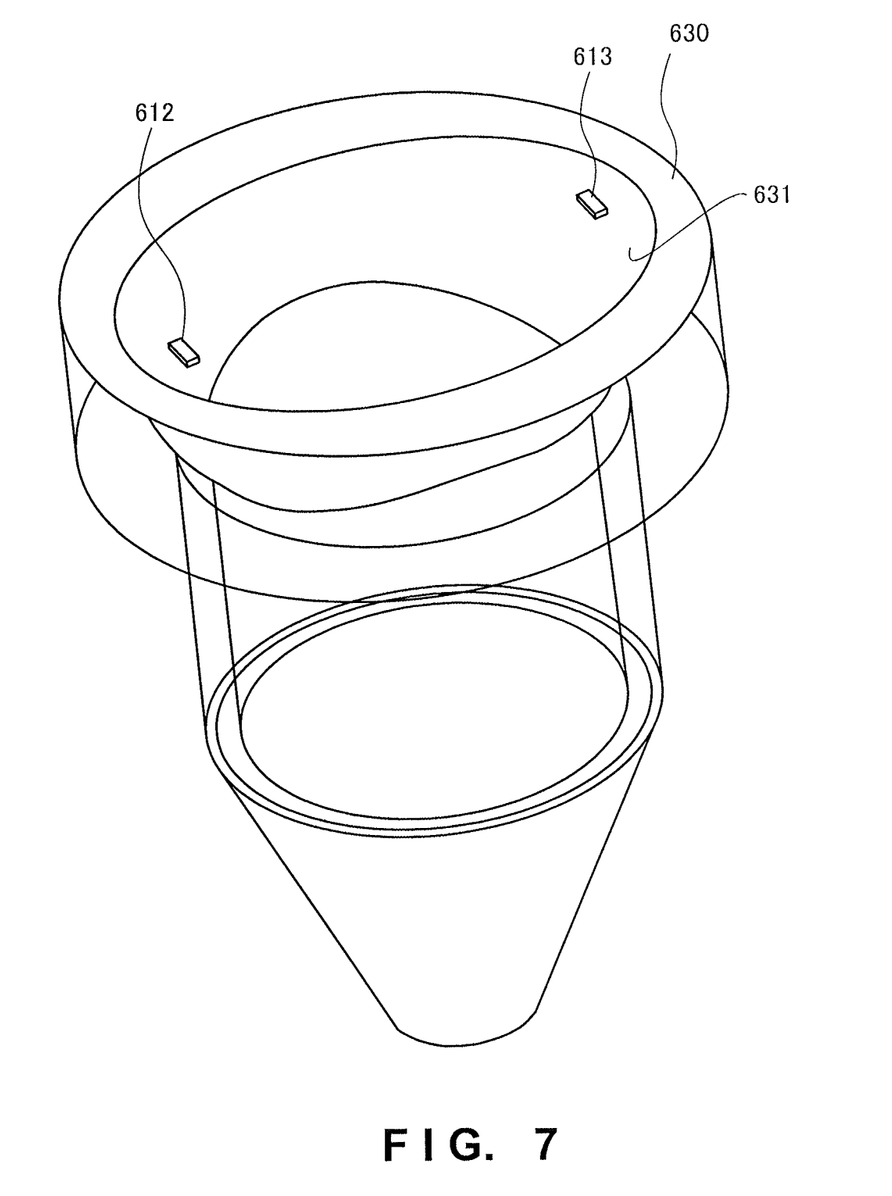
FIG. 7 is a sectional view showing the arrangement of the optical processing head according to the third embodiment of the present invention.

An optical processing head 600 according to the third embodiment of the present invention will be described with reference to FIG. 6. FIG. 6 is a perspective view for explaining the internal arrangement of the optical processing head 600 according to this embodiment. FIG. 7 is a partial enlarged view. The optical processing head 600 according to the third embodiment is different from the optical processing head according to the second embodiment in that it includes an inspection unit 630 different in the inner surface shape from the inspection unit 230. The remaining arrangement and operation are the same as those in the second embodiment, so the same reference numerals denote the same arrangement and operation and a detailed description thereof will not be repeated.

The inspection unit 630 internally has a curved surface 631 of a shape conforming to the outer surface of a rotational ellipsoid. A ray emitter 612 for inspection and a light receiver 613 are arranged at two focus positions of the rotational ellipsoid. In this embodiment, no shielding plate need be provided around the ray emitter 612 for inspection. However, the shielding plate may also be provided. In this case, noise of a detection signal can be satisfactorily reduced.

Figure 8:
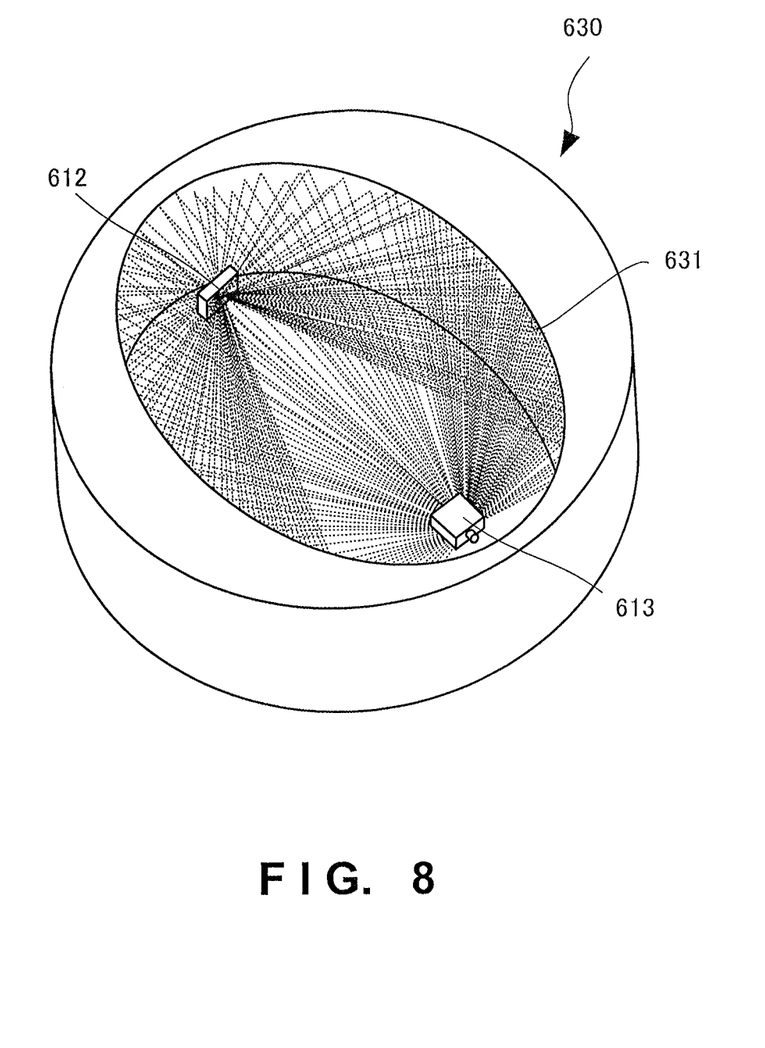
FIG. 8 is a sectional view showing the arrangement of a ray emitter for inspection and a light receiver, and a ray path between them according to the third embodiment of the present invention.

FIG. 8 is a ray diagram between the ray emitter 612 for inspection and the light receiver 613 in the optical processing head 600 according to this embodiment. As is apparent from FIG. 8, the light receiver 613 receives all rays for inspection. That is, there is an effect of efficiently using inspection rays for inspection.

With the above-described arrangement, a line segment connecting the ray emitter 612 for inspection and the light receiver 613 can be perpendicular to the optical axis. Accordingly, the optical processing head 600 that is compact in the optical axis direction can be implemented.

Fourth Embodiment

Figure 9:
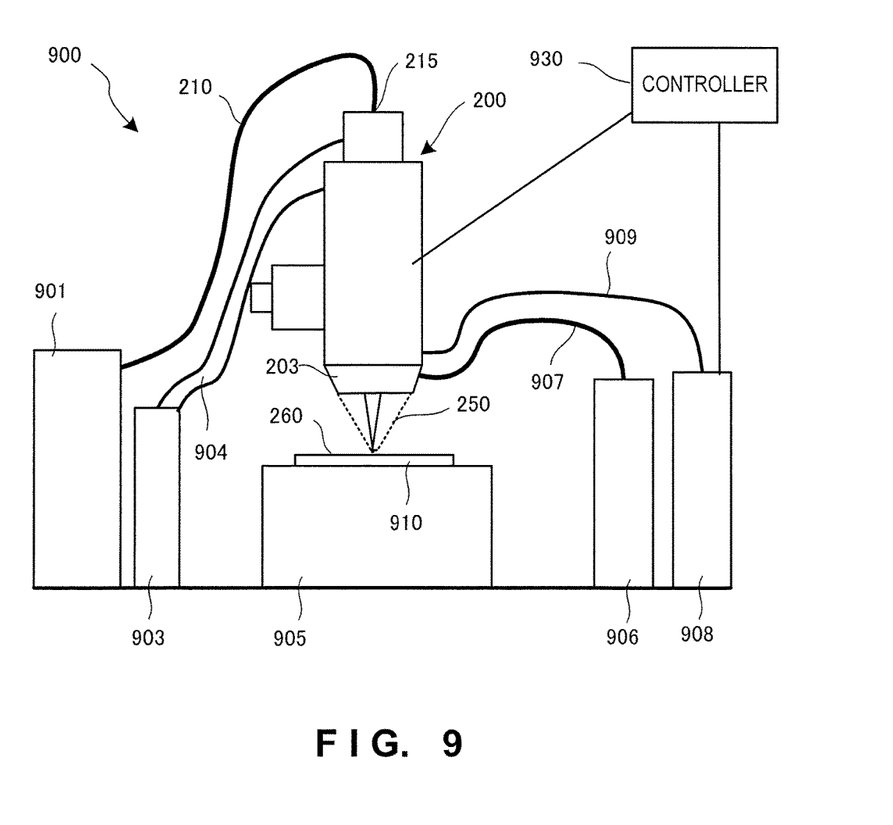
FIG. 9 is a view showing the arrangement of an optical processing apparatus according to the fourth embodiment of the present invention.

An optical processing apparatus 900 according to the fourth embodiment of the present invention will be described with reference to FIG. 9. The optical processing apparatus 900 is an apparatus that includes one of the optical processing heads 100, 200, and 600 explained in the above-described embodiments, and generates a three-dimensional shaped object (or overlay welding) by melting a material by heat generated by condensed light. Here, the optical processing apparatus 900 including an optical processing head 200 will be explained as an example.

<<Apparatus Arrangement>>

In addition to the optical processing head 200, the optical processing apparatus 900 includes a light source 901, a light transmitting portion 210, a coolant supply device 903, a coolant supply portion 904, a stage 905, a material supply device 906, a material supply portion 907, a gas supply device 908, a gas supply portion 909, and a controller 930.

The light source 901 can be a laser, an LED, a halogen lamp, a xenon lamp, an incandescent lamp, or the like. The wavelength of a ray is, for example, 1,060 nm, but is not limited to this.

The coolant supply device 903 stores, for example, water as a coolant, and supplies the coolant by a pump to the optical processing head 200 via the coolant supply portion 904.

The coolant supply portion 904 is a resin or metal hose having an inner diameter of ϕ2 to 6. The coolant is supplied into the optical processing head 200, circulated inside it, and returned to the coolant supply device 903, thereby suppressing the temperature rise of the optical processing head 200. The coolant supply amount is, for example, 1 to 10 L/min.

The stage 905 is, for example, an X stage, an X-Y stage, or an X-Y-Z stage, and can operate the respective axes (X, Y, and Z). The material supply device 906 supplies a material to a nozzle 203 via the material supply portion 907. Examples of the material are a metal particle, a resin particle, a metal wire, and a resin wire. The material supply device 906 can simultaneously supply even a carrier gas.

The material supply portion 907 is, for example, a resin or metal hose, and guides, to the nozzle 203, a powder flow prepared by mixing a material in a carrier gas. However, when the material is a wire, no carrier gas is necessary. The nozzle 203 ejects a material toward a process surface 260.

The gas supply device 908 supplies a purge gas to the optical processing head 200 through the gas supply portion 909. The purge gas is, for example, nitrogen, argon, or helium. However, the purge gas is not limited to this and may also be another gas as long as the purge gas is an inert gas. The purge gas supplied to the optical processing head 200 is ejected from the nozzle 203 along the above-described ray.

Although not shown, the optical processing apparatus 900 includes an orientation control mechanism and position control mechanism that control the orientation and position of the optical processing head 200.

<<Apparatus Operation>>

Next, the operation of the optical processing apparatus 900 will be explained. A shaped object 910 is created on the stage 905.

The purge gas is ejected from the nozzle 203 to the process surface 260. Thus, the peripheral environment of the molten pool is purged by the purge gas. By selecting an oxygen-free inert gas as the purge gas, oxidization of the process surface 260 can be prevented.

The optical processing head 200 is cooled by the coolant supplied from the coolant supply device 903 through the coolant supply portion 904, suppressing the temperature rise during processing.

By scanning the optical processing head 200 along the process surface 260 at the same time as the above-described series of operations, desired shaping can be performed while depositing the material. That is, this apparatus can implement overlay welding or three-dimensional shaping.

The controller 930 also functions as a purge controller that acquires, from the inspection unit 230, the status of a scattering object inside the optical processing head 200, controls the gas supply device 908 in accordance with this status, and changes the amount of a purge gas to be sprayed to the process surface 260.

Figure 10:
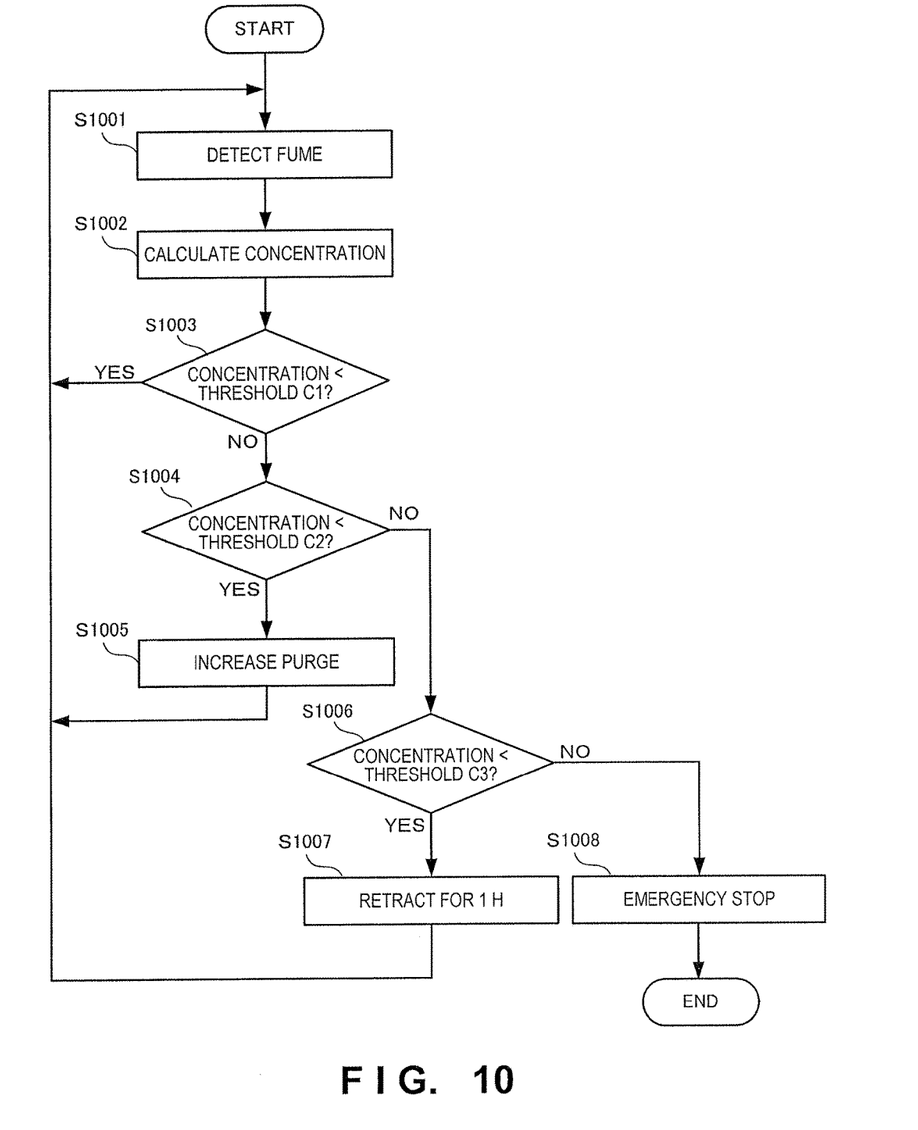
FIG. 10 is a flowchart showing the sequence of control by the optical processing apparatus according to the fourth embodiment of the present invention.

FIG. 10 is a flowchart showing the sequence of this control. This flowchart represents that four stages of control are performed in accordance with the amount of a scattering object by using three thresholds (threshold C1<threshold C2<threshold C3).

If a scattering object (fume) is detected in step S1001, the process advances to step S1002 to calculate the concentration. In step S1003, the calculated concentration is compared with the threshold C1. If the concentration is lower than the threshold C1, no problem occurs, so the process returns to step S1001. If the concentration is higher than the threshold C1, it is compared with another threshold C2 in step S1004. If the concentration is lower than the threshold C2, the process advances to step S1005 to cope with the scattering object by increasing the purge gas. If the concentration of the scattering object is higher than the threshold C2, the process advances to step S1006 to further compare the concentration with the threshold C3. If the concentration of the scattering object is lower than the threshold C3, the process advances to step S1007 to stop the optical processing apparatus 900 for 1 h or retract a workpiece for 1 h. If the concentration of the scattering object becomes higher than the threshold C3, the process advances to step S1008 to perform emergency stop.

As described above, according to the fourth embodiment, damage to a condensing optical system device 201 or the optical processing head 200 can be reduced.

Other Embodiments

The present invention has been described above with reference to the embodiments. However, the present invention is not limited to those embodiments. Various changes understandable by those skilled in the art within the scope of the present invention can be made for the arrangements and details of the present invention. The present invention also incorporates a system or apparatus that somehow combines different features included in the respective embodiments.

The present invention is applicable to a system including a plurality of devices or a single apparatus. The present invention is also applicable even when a control program for implementing the functions of the embodiments is supplied to the system or apparatus directly or from a remote site. Hence, the present invention also incorporates the program installed in a computer to implement the functions of the present invention on the computer, a medium storing the program, and a WWW (World Wide Web) server that causes a user to download the program. Especially, a non-transitory computer readable medium storing a program for causing a computer to execute processing steps included in the above-described embodiments falls within the scope of the present invention.

The invention claimed is:

1. An optical processing head that performs processing by condensing, on a process surface, a ray emitted by a light source for processing, comprising:
   a cylindrical housing that surrounds a ray for processing emitted by the light source for processing;
   a condenser lens that condenses the ray for processing to a downstream side of the cylindrical housing toward the process surface;
   a ray emitter for inspection that is incorporated in said cylindrical housing, said ray emitter being arranged downstream of said condenser lens and arranged outside a path of the ray for processing;
   a light receiver that is incorporated in said cylindrical housing, said light receiver being arranged downstream of said condenser lens, being arranged outside the path of the ray for processing, and being arranged for receiving a ray for inspection emitted by said ray emitter for inspection,
   a mirror for observation that is disposed upstream of said condenser lens; and
   an image sensor that senses an image of the process surface using reflection from said mirror for observation,
   wherein one of a contamination of an inner surface of said cylindrical housing and a concentration of a scattering object flowing into said cylindrical housing is inspected by using a signal acquired from said light receiver, and
   wherein said light receiver is disposed on the downstream side of the ray emitter for inspection toward the process surface.

2. The optical processing head according to claim 1, wherein at least part of the inner surface of said cylindrical housing is a curved surface so as to reflect the ray for inspection by the inner surface of said cylindrical housing and condense the ray for inspection to said light receiver.

3. The optical processing head according to claim 2, wherein at least one of sections of the curved surface passing through both said ray emitter for inspection and said light receiver is an ellipse.

4. The optical processing head according to claim 3, wherein said ray emitter for inspection and said light receiver are arranged at two focus positions of the ellipse, respectively.

5. The optical processing head according to claim 4, wherein
   the curved surface has a shape conforming to an outer surface of a rotational ellipsoid, and
   said ray emitter for inspection and said light receiver are arranged at two focus positions, respectively, of the rotational ellipsoid.

6. The optical processing head according to claim 2, wherein
   the curved surface has a columnar shape having a diameter D using an optical axis of the ray for processing as a center, and
   letting θ be an angle defined by the optical axis and a line segment connecting said ray emitter for inspection and said light receiver, and L be a distance between said ray emitter for inspection and said light receiver, the following equation is established:

$D/L = 2/\tan \theta$.

7. The optical processing head according to claim 1, wherein a concentration of a scattering object flowing into said cylindrical housing is inspected based on a temporal change of a signal acquired from said light receiver.

8. The optical processing head according to claim 1, wherein a contamination of the inner surface of said cylindrical housing is inspected based on a change, from a reference value, of a signal acquired from said light receiver.

9. An optical processing apparatus comprising:
   an optical processing head defined in claim 1; and
   a purge controller that changes, based on the signal, an amount of a purge gas ejected to the process surface.

10. A method of controlling an optical processing apparatus comprising an optical processing head according to claim 1, wherein the processing apparatus performs processing by condensing, on a process surface, a ray emitted by a light source for processing, the method comprising:
   changing, based on a signal acquired from said light receiver, an amount of a purge gas ejected to the process surface.

* * * * *